United States Patent
Morazzoni et al.

(10) Patent No.: US 8,569,455 B2
(45) Date of Patent: Oct. 29, 2013

(54) CLONING, YEAST EXPRESSION, PURIFICATION AND BIOLOGICAL ACTIVITY OF THE EXTENSION REGION OF THE SOYBEAN 7S GLOBULIN ALFA' SUBUNIT INVOLVED IN HEP G2 CELL CHOLESTEROL HOMEOSTASIS

(75) Inventors: Paolo Morazzoni, Milan (IT); Antonella Riva, Milan (IT); Cesare Ponzone, Milan (IT); Davide Berlanda, Milan (IT); Marcello Duranti, Milan (IT); Alessandro Consonni, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 13/378,605

(22) PCT Filed: Jun. 16, 2010

(86) PCT No.: PCT/EP2010/003627
§ 371 (c)(1),
(2), (4) Date: Mar. 12, 2012

(87) PCT Pub. No.: WO2010/145820
PCT Pub. Date: Dec. 23, 2010

(65) Prior Publication Data
US 2012/0172316 A1    Jul. 5, 2012

(30) Foreign Application Priority Data

Jun. 17, 2009 (EP) ................................. 09162939

(51) Int. Cl.
*C07K 14/415* (2006.01)
*C12P 21/04* (2006.01)
*A61K 38/16* (2006.01)

(52) U.S. Cl.
USPC ................... 530/350; 435/71.1; 514/7.4

(58) Field of Classification Search
None
See application file for complete search history.

(56) References Cited

FOREIGN PATENT DOCUMENTS

WO     WO 03/063608 A1     8/2003
WO     WO 2007/147064 A2   12/2007

OTHER PUBLICATIONS

Cregg JM et al. Recombinant Protein Expression in *Pichia pastoris*. 2000. Molecular Biotechnology. 16:1 p. 23-52.*
M. Lovati, et al., "Biological Activity of a Truncated Form of the Soybean 7S Globulin Alpha Subunit on Cell Cholesterol Homeostasis", Atherosclerosis Supplements 2009, Jun. 16, 2009, vol. 10, No. 2.
M. Lovati, et al., XV International Symposium on AtherosclerosisTimetable for Tuesday, Jun. 16, 2009, pp. 75-94.
Duranti Marcello et al., "The Alpha' Subunit From Soybean 7S Globulin Lowers Plasma Lipids and Upregulates Liver Beta-VLDL Receptors in Rat Fed a Hypercholesterolemic Diet", Journal of Nutrition, Jun. 2004, pp. 1334-1339, vol. 134, No. 6.

* cited by examiner

*Primary Examiner* — David J Steadman
*Assistant Examiner* — Paul Holland
(74) *Attorney, Agent, or Firm* — Arent Fox LLP

(57) ABSTRACT

A truncated form of α' chain (eα'), the soybean 7S globulin, active in controlling the cholesterol and triglyceride homeostasis in in vitro and in vivo models, was cloned and expressed in the yeast *Pichia pastoris*. The recombinant polypeptide spanned 142 amino acid residues from the N-terminal side and included the N-terminal extension region of the soybean alpha' subunit. The eα' polypeptide was purified by conventional biochemical techniques and its potential to modulate the activity of the LDL-receptor was evaluated in a human hepatoma cell line (Hep G2) by monitoring the uptake and degradation of labeled LDL.

3 Claims, 4 Drawing Sheets

Figure 2

```
α'e    AVEEEEECEEGQIPRPRPQHPERERQQHGEKEEDEGEQPRPFPFPRPRQPHQEEEHEQKE   60
α'     -VEEEEECEEGQIPRPRPQHPERERQQHGEKEEDEGEQPRPFPFPRPRQPHQEEEHEQKE   59
        ***********************************************************

α'e    EHEWHRKEEKHGGKGSEEEQDEREHPRPHQPHQKEEEKHEWQHKQEKHQGKESEEEEEDQ  120
α'     EHEWHRKEEKHGGKGSEEEQDEREHPRPHQPHQKEEEKHEWQHKQEKHQGKESEEEEEDQ  119
        ************************************************************

α'e    DEDEEQDKESQESEGSESQREP--------------------------------------  142
α'     DEDEEQDKESQESEGSESQREPRRHKNKNPFHFNSKRFQTLFKNQYGHVRVLQRFNKRSQ  179
        *********************

α'e    ------------------------------------------------------------
α'     QLQNLRDYRILEFNSKPNTLLLPHHADADYLIVILNGTAILTLVNNDDRDSYNLQSGDAL  239

α'e    ------------------------------------------------------------
α'     RVPAGTTFYVVNPDNDENLRMIAGTTFYVVNPDNDENLRMITLAIPVNKPGRFESFFLSS  299

α'e    ------------------------------------------------------------
α'     TQAQQSYLQGFSKNILEASYDTKFEEINKVLFGREEGQQQGEERLQESVIVEISKKQIRE  359

α'e    ------------------------------------------------------------
α'     LSKHAKSSSRKTISSEDKPFNLGSRDPIYSNKLGKLFEITQRNPQLRDLDVFLSVVDMNE  419

α'e    ------------------------------------------------------------
α'     GALFLPHFNSKAIVVLVINEGEANIELVGIKEQQQRQQQEEQPLEVRKYRAELSEQDIFV  479

α'e    ------------------------------------------------------------
α'     IPAGYPVMVNATSDLNFFAFGINAENNQRNFLAGSKDNVISQIPSQVQELAFPRSAKDIE  539

α'e    ---------------------------------
α'     NLIKSQSESYFVDAQPQQKEEGNKGRKGPLSSILRAFY  577
```

Figure 2A

α'e (SEQ ID 1)

```
AVEEEEECEEGQIPRPRPQHPERERQQHGEKEEDEGEQPRPFPFPRPRQPHQEEEHEQKE  60
EHEWHRKEEKHGGKGSEEEQDEREHPRPHQPHQKEEEKHEWQHKQEKHQGKESEEEEEDQ 120
DEDEEQDKESQESEGSESQREP------------------------------------ 142
```

Figure 2B

α' (SEQ ID 2)

```
-VEEEEECEEGQIPRPRPQHPERERQQHGEKEEDEGEQPRPFPFPRPRQPHQEEEHEQKE  59
EHEWHRKEEKHGGKGSEEEQDEREHPRPHQPHQKEEEKHEWQHKQEKHQGKESEEEEEDQ 119
DEDEEQDKESQESEGSESQREPRRHKNKNPFHFNSKRFQTLFKNQYGHVRVLQRFNKRSQ 179
QLQNLRDYRILEFNSKPNTLLLPHHADADYLIVILNGTAILTLVNNDDRDSYNLQSGDAL 239
RVPAGTTFYVVNPDNDENLRMIAGTTFYVVNPDNDENLRMITLAIPVNKPGRFESFFLSS 299
TQAQQSYLQGFSKNILEASYDTKFEEINKVLFGREEGQQQGEERLQESVIVEISKKQIRE 359
LSKHAKSSSRKTISSEDKPFNLGSRDPIYSNKLGKLFEITQRNPQLRDLDVFLSVVDMNE 419
GALFLPHFNSKAIVVLVINEGEANIELVGIKEQQQRQQQEEQPLEVRKYRAELSEQDIFV 479
IPAGYPVMVNATSDLNFFAFGINAENNQRNFLAGSKDNVISQIPSQVQELAFPRSAKDIE 539
NLIKSQSESYFVDAQPQQKEEGNKGRKGPLSSILRAFY 577
```

Fig. 3 - Panel A
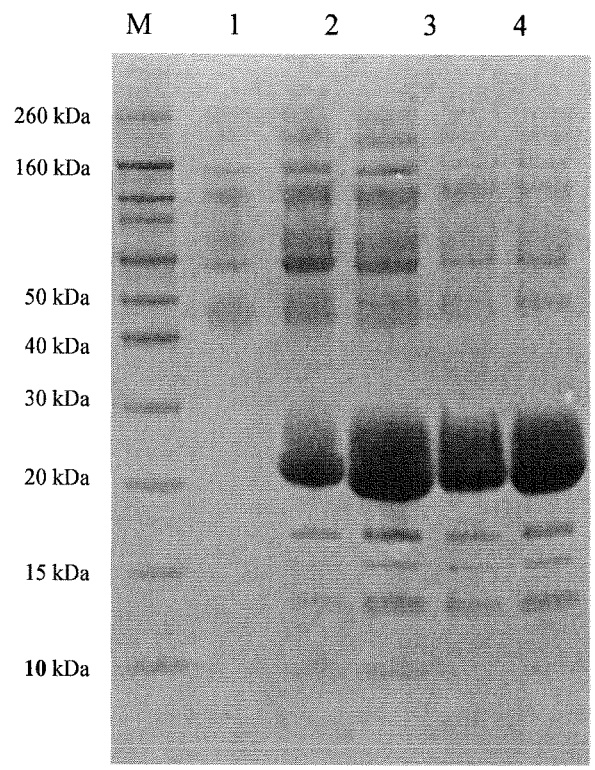
Fig. 3 - Panel B
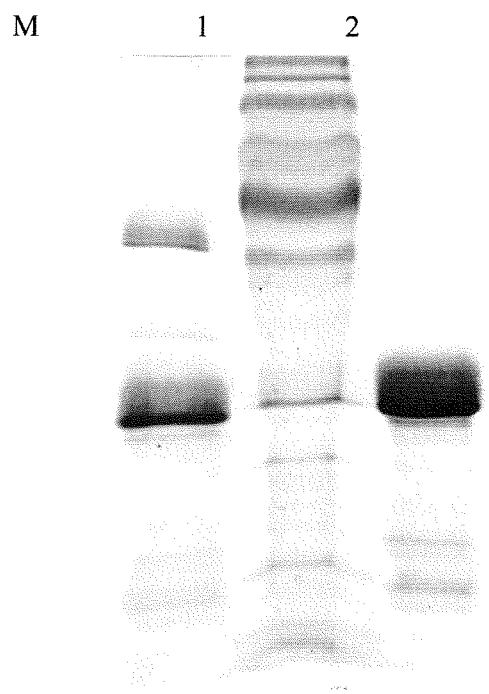

CLONING, YEAST EXPRESSION, PURIFICATION AND BIOLOGICAL ACTIVITY OF THE EXTENSION REGION OF THE SOYBEAN 7S GLOBULIN ALFA' SUBUNIT INVOLVED IN HEP G2 CELL CHOLESTEROL HOMEOSTASIS

SEQUENCE LISTING

The instant application contains a Sequence Listing which has been submitted in ASCII format via EFS-Web and is hereby incorporated by reference in its entirety. Said ASCII copy, created on Mar. 8, 2012, is named 10050600.txt and is 8,065 bytes in size.

The present invention refers to a recombinant α' fragment of the soybean 7S globulin corresponding to the N-terminal hydrophilic fragment of the natural α' subunit, to a process for its preparation and to compositions containing it as an active ingredient useful for controlling the cholesterol and triglyceride homeostasis.

BACKGROUND OF THE INVENTION

The role of dietary soybean proteins in the control of lipidemic levels of hypercholesterolemic patients is a widely accepted issue [1]. In previous studies [2-4], the direct involvement of one subunit of the soybean 7S globulin, the α' subunit, in the up-regulation of the LDL-receptor was demonstrated in in vitro and in vivo systems, suggesting that biologically active (poly)peptides, capable of modulating cholesterol homeostasis, are likely to be produced by cell enzyme processing.

The native 7S globulin is composed of three randomly assorted polypeptide chains, the α', α and β subunits [5], encoded by different genes. The mature α' (Accession N. P11827 UniProtKB/Swiss-Prot database) and α chains (Accession N. P13916 UniProtKB/Swiss-Prot database) share an extended N-terminal region of about 145 amino acid residues which is missing in the β subunit (Accession N. P25974 UniProtKB/Swiss-Prot database). Based on the peculiar amino acid sequence of the α' extension region, this subunit was purified by metal affinity chromatography and orally administered to hypercholesterolemic rats, thus allowing to show both its plasma lipid-lowering properties and up-regulation of liver β-VLDL receptors [4]. On the other hand, since the molecular weight of the α' subunit is around 71 kDa [6], it seems unlikely that it may cross in vivo the intestinal barrier with no modification.

For this reason, our research has been directed to seeking the amino acid sequence/s of α' subunit responsible for the pharmacological effect. Since the core regions of the three subunits have more similar amino acid sequences, it is conceivable that the biological activity should reside in one or more (poly)peptides of the extension region. In principle, the localized but significant amino acid differences between the extension regions of the α' and α chains would limit the number of peptides responsible for the biological activity.

From these previous statements, the first strategy pursued was to test the effect of both polypeptides in Hep G2 cells, obtained from the in vitro digestion (pepsin/trypsin) of Croksoy$^R$70, an isoflavone-free soybean concentrate routinely employed in the dietary treatment of hypercholesterolemic patients [7-8], and synthetic peptides, corresponding to specific amino acid sequences that differed between the 7S soybean globulin subunits, on the LDL-receptor (LDL-R) modulation. The results obtained in these studies pointed out that a marked LDL-R up-regulation could be induced in HepG2 cells exposed to enzyme digestion products of Croksoy$^R$70 with MW ranging from 3,000 to 20,000 Da, as well as to a small synthetic peptide (2,271 Da) from 7S soybean globulin added to cells at a concentration of $10^{-4}$M [9]. The study obtained with small peptides is still currently under investigation and have not been conclusive so far [10].

The cholesterol and triglyceride lowering capacity of soybean proteins is a consolidated issue. The soybean protein diet is currently the most potent dietary tool for treating hypercholesterolemic patients, thus providing a unique opportunity for the management of adults and very young subjects. Moreover, it is clearly established that the plasma cholesterol reduction is greater in patients having a high baseline degree of cholesterolemia [14].

The hypothesis that proteins per se reduce blood cholesterol arose from experimental studies indicating that a shift from animal to plant proteins in the diet activates the LDL receptor system in the liver of laboratory animals [15], as well as in circulating lymphomonocytes of hypercholesterolemic patients [16]. To identify the soybean protein components responsible for the cholesterol lowering effect, in vitro studies were carried out with a human hepatoma cell line that is highly sensitive to factors regulating LDL-receptor expression and cholesterol biosynthesis/breakdown. The purified α' subunit from the 7S soybean globulin was found to up-regulate LDL-receptors in Hep G2 cells [3] and this finding was confirmed in cholesterol-fed rats [4]. Although these data support the hypothesis that the protein moiety is responsible for the observed biological effect, arguments may be raised to α' chain in vivo biological fate, since peptides and amino acids are normally produced by the action of gastric and/or intestinal proteolytic enzymes. However, an increasing number of animal and plant (poly)peptides is being claimed to play relevant regulatory functions, often attributed to antioxidant, anti-proliferative and anti-inflammatory effects [17]. As far as soybean is concerned, experimental evidence clearly indicates the possibility that peptides and even small compact proteins, such as the Bowman-Birk inhibitor, may be adsorbed [18], thus eliciting a number of effects, including anti-cancer, anti-inflammatory, radio-protective ones [19]. Also genetically modified soybean (poly)peptides have been shown to trigger biological responses, such as hypotensive effects [20]. Recently, a LDL-R transcription stimulating peptide (FVVNATSN) (SEQ ID NO: 3), deriving from the 7S globulin β chain, has been identified from a soybean hydrolysate prepared by a protease from Bacillus amyloliquefaciens and then by chemical synthesis [21]. In this case, an increased LDL-R transcription (+148%) was detected in Hep G2 cells exposed to the peptide at a concentration of 100 μM. Other peptides arising from the 11 S globulin have been shown to exert similar but lower activity [21].

It would be desirable to make available shorter polypeptides maintaining or even improving the biological properties of the full length protein.

DESCRIPTION OF THE INVENTION

It has now been found that the so-called α' Extension Region of Soybean 7S Globulin corresponding to the N-terminal side thereof has advantageous biological activity and proved to be even more effective on LDL uptake and degradation than the full size α' chain.

The invention provides therefore said α' Extension Region, which will be hereinafter referred to as eα', as well as a process for its preparation by cloning, yeast expression and purification of the recombinant polypeptide containing the N-terminal extension region of the soybean α'subunit.

To this purpose the heterologous expression of the N-terminal fragment of the α' chain was undertaken. The objective was achieved in secretion-competent yeast cells of yeast *Pichia pastoris*. The recombinant polypeptide was purified and its biological activity assessed in HepG2 cells. By the use of this biotechnological approach, adequate amounts of the recombinant polypeptide could be obtained to be tested in in vitro trials and also in in vivo experiments.

DESCRIPTION OF THE FIGURES

FIG. 2 Sequence alignment of the recombinant polypeptide (eα') (SEQ ID NO: 1) and wild type soybean α' (SEQ ID NO: 2) subunit. Stars indicate identical amino acid residues in the two sequences.

FIG. 2A Sequence of the recombinant polypeptide (ea)' (SEQ ID NO: 1)

FIG. 2B Sequence of the wild type soybean a' subunit (SEQ ID NO: 2)

FIG. 3A. SDS-PAGE under reducing conditions of recombinant *Pichia pastoris* culture:
Lane M: Molecular Weight Marker
Lane 1: TCA-precipitated culture supernatant (cell free) before induction with methanol.
Lane 2: TCA-precipitated culture supernatant (cell free) after 1 h of induction with methanol.
Lane 3: TCA-precipitated culture supernatant (cell free) after 8 h of induction with methanol.
Lane 4: TCA-precipitated culture supernatant (cell free) after 19 h of induction with methanol.
Lane 5: TCA-precipitated culture supernatant (cell free) after 25 h of induction with methanol.

FIG. 3B. SDS-PAGE under reducing conditions of eα' purification steps:
Lane M: Molecular Weight Marker
Lane 1: lyophilized powder of fermentation broth
Lane 2: DEAE-cellulose 150 mM NaCl eluted fraction
Lane 3: DEAE-cellulose 250 mM NaCl eluted fraction

DETAILED DESCRIPTION OF THE INVENTION

Figure 1:
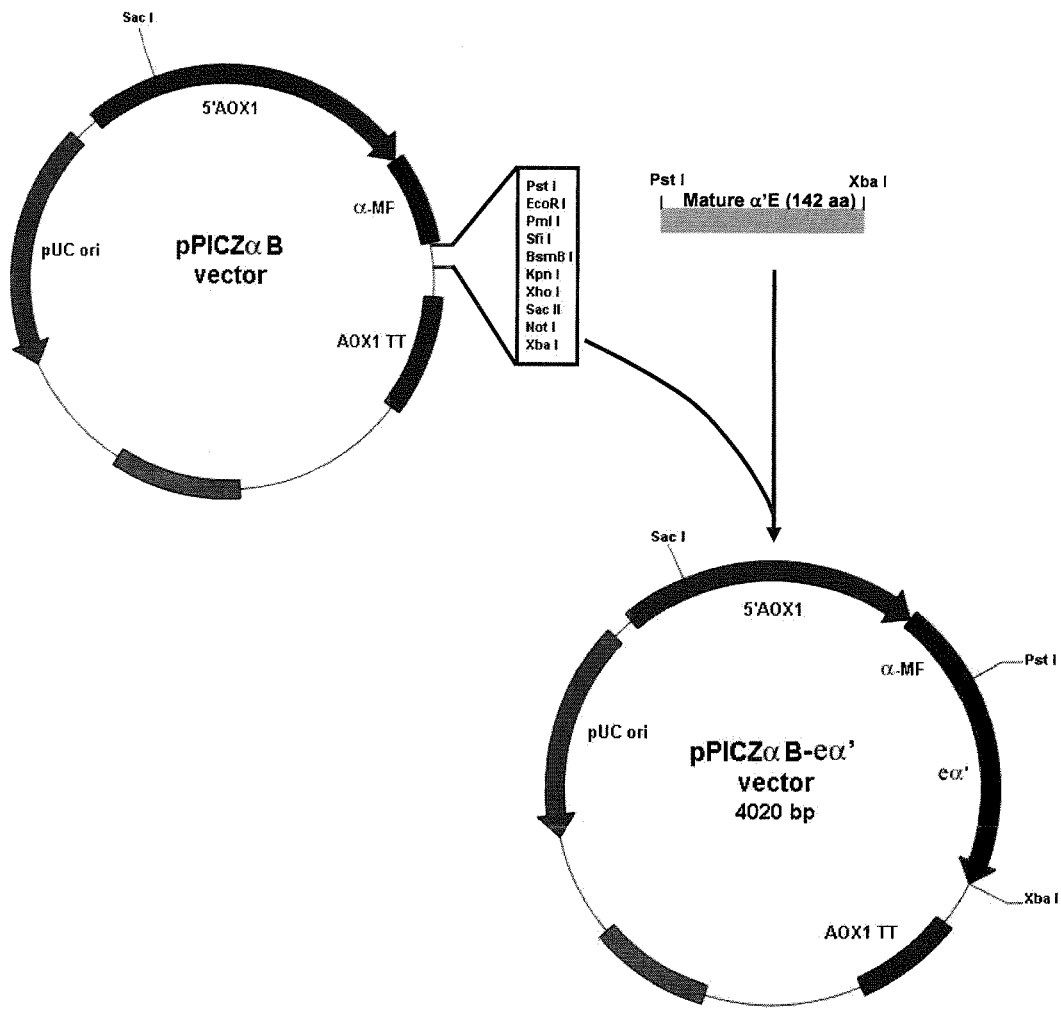
FIG. 1 Overview of the pPICZαB-eα' construct. Expression of eα' is driven by the AOX (Alcohol OXidase) methanol-inducible promoter (5'AOX1); the α-Mating Factor (α-MF) promotes secretion of the recombinant protein to the medium; AOX1 TT: AOX transcription termination region. Sh ble gene confers resistance to zeocin; pUC Ori: origin of replication for high number plasmid copy in *E. coli*. The other abbreviations refer to the cleavage positions of restriction enzymes; bp: base pair.

The invention will now be described in detail in the following experimental section.

Materials and Methods

Yeast, Bacterial Strains and Chemicals.

*Pichia pastoris* X33 (WT) strain (Invitrogen, San Diego, Calif.) was used for yeast expression. The bacterial strain utilized for genetic manipulations was *E. coli* XL1-Blue (Invitrogen, San Diego, Calif.). Restriction enzymes Pst I and Xba I were purchased from Roche (Indianapolis, Ind.), Sac I from Fermentas (Ontario, Canada) Taq DNA polymerase was purchased from Invitrogen (San Diego, Calif.). Zeocin was purchased from Invivogen (San Diego, Calif.). The oligonucleotides for PCR were obtained from Primm (Milano, Italy). Peptone, tryptone, yeast extract and agar were purchased from Becton Dickinson and Company (Sparks, Md.). Glucose and Sorbitol were purchased from Sigma (St. Louis Mo.). Dialysis Membranes were purchased from Spectrum Laboratories (Rancho Dominguez, Calif.). DEAE resin was purchased from Whatman (Maidstone, England). NiNTA resin was purchased from Qiagen (Hilden, Germany). Symmetry C4 HPLC Column was purchased from Waters (Milford, Mass.).

Other chemicals were reagent grade from Sigma (St. Luis, Mo.) or from Merck (Darmstadt, Germany).

Media and Growth Conditions.

*P. pastoris* X33 strain was cultured in YPD (Yeast Peptone Dextrose) complete medium (2% peptone, 1% yeast extract, 2% glucose). The Mut$^+$ transformants were selected in plates containing YPD, agar 1.5%, 100 mg/mL zeocin. All yeast cultures were maintained at 30° C. For heterologous protein detection, Zeo$^r$-Mut$^+$ transformants were cultured to an optical density of 5 at 600 nm in YPS (Yeast Peptone Sorbitol) medium (2% peptone, 1% yeast extract, 2% sorbitol). Then methanol was added to 1% final concentration. All bacterial transformants were selected in plates of low-salt LB (Luria-Bertani) medium containing zeocin (1% tryptone, 0.5% yeast extract, 0.5% sodium chloride, 1.5% agar, 25 mg/mL zeocin). All bacterial cultures were maintained at 37° C.

Construction of eα' gene expression vector. The eα' gene was amplified by PCR on an expression *Pichia pastoris* plasmid DNA template (pPICZαB) containing an insert (tα') comprising the sequence of interest (eα'). The oligonucleotide 5'-GAAAAGATAGATTAAAG CTGCAGTGGAGGAAG-3' (SEQ ID NO: 4) was designed to generate PstI restriction site at the 5' end of eα' gene. This mutation resulted in an alanine residue insertion in the N-terminal position of eα'. A second oligonucleotide 5'-CCCT-TCTTATTCTT TCTAGATCATGGTTCTCTTTGAGACTC-3' (SEQ ID NO: 5) was designed to generate XbaI restriction site at the 3' end of eα' gene. Both oligonucleotides were dissolved in mQ sterile water. The PCR reaction mixture consisted of 0.5 mM primers, 0.8 mM dNTPs (Eppendorf, Hamburg, Germany), 30 ng template (pPICZαB/tα'), 2.5 U Taq DNA Polymerase, PCR buffer (final composition: 50 mM KCl, 1.5 mM MgCl$_2$, 20 mM Tris-Cl, pH 8.4 and mQ sterile water to a final volume of 25 mL). PCR amplification was carried out on a Perkin Elmer Geneamp PCR System 2400 thermocycler (Perkin Elmer Corp., Wellesley, Mass.) using the following conditions: start at 94° C. for 10 min; 30 cycles at 94° C. for 40 sec, 60° C. for 40 sec, 72° C. for 20 sec; final extension 72° C. for 10 min and maintained at 4° C. The PCR product of 465 by was enzymatically digested to a full size construct of 423 by and it was cloned into pPICZαB vector resulting in the pPICZαB-eα' construct and transformed in XL1-Blue *E. coli* cells. Positives clones were selected on semisolid LB media containing tetracycline and zeocin. One of these clones was sequenced by Primm (Milano, Italy) to ensure that no mutation occurred in pPICZαB-eα' construct sequence. Twenty μg pPICZαB-eα' construct and 30 gg expression vector pPICZαB (negative control) were linearized by digestion with the restriction enzyme SacI and then purified.

Transformation of pPICZαB-eα' in *P. pastoris* genome. Wild type (wt) yeast cells were transformed by electroporation with 20 μg linearized pPICZαB-eα' construct and 30 μg linearized pPICZαB on an Eppendorf (Hamburg, Germany) electroporator 2510 apparatus set at 1.5 kV. Transformants were first selected by plating on YPD plates containing 100 mg/mL of zeocin. In order to verify the integration of our construct into transformed *P. pastoris* genome, the Dneasy Plant Mini Kit (QIAGEN, Hilden, Germany) was used to extract genomic DNA. Genomic DNA was used as template to verify the insertion of the construct at the alcohol oxidase promoter (AOX1) site by PCR using 5'AOX1 (5''-GACTG- GTTCCAATTGACAAGC-3") (SEQ ID NO: 6) and 3'AOX1 primers (5"-GCAAATGGCATTCTGAGATCC-3") (SEQ ID NO: 7). The PCR reaction mixture consisted of 0.5 mM primers, 0.25 mM dNTPs, 100 ng for genomic template, 2.5 U Taq DNA Polymerase, PCR buffer (final composition as above). PCR reaction was performed using the following conditions: start at 94° C. for 10 min; 30 cycles at 94° C. for 40 s, 60° C. for 40 s, 72° C. for 20 s; final extension 72° C. for 10 min and maintained at 4° C.

Transformant Clone Selection.

Eighteen Zeo$^+$ transformants and one transformant containing pPICZαB expression vector (negative control) were grown in 50 mL of YPS medium at 30° C. in a shaking (180 rpm) incubator to an $OD_{600}$=5. The inducing phase was triggered by adding methanol to 1% final concentration and prolonged for 24 hours. Aliquots of the supernatants were examined for expression of eα' by SDS-PAGE. The clone transformant with the highest eα' expression was selected for fermenter scale production of the recombinant protein.

Expression of eα': Fermenter Scale

For massive production, the selected clone was grown in 14 L fermenter (Chemap, Switzerland), according to Invitrogen's "*Pichia* Fermentation Process Guidelines" (Version B, 053002). Inoculum culture is prepared on YNB medium ($KH_2PO_4$ 2.0 g; $(NH_4)_2SO_4$ 10.0 g; $MgSO_4$ $7H_2O$ 1.0 g; NaCl 0.2 g; $CaCl_2$ 0.2 g; Glycerol 100% 10.0 g; KOH to pH 5.2; Distilled water to 1.0 L) in unbaffled shake flasks. After incubation for approx. 24 hours at 30° C. at 250 rpm, 1.0 L of seed culture is used to inoculate the fermenter, prepared with 8.5 L of Basal Salt Medium ($H_3PO_4$ 85% 227 mL; $CaSO_4$ $2H_2O$ 7.9 g; $K_2SO_4$ 155 g; $MgSO_4$ $7H_2O$ 127 g; KOH 35 g; Glycerol 100% 340 g; Distilled water to 8.5 L; pH adjusted to 5.0 with $NH_4OH$ after sterilization). Both cited culture media are supplemented with biotin and inositol (1 mg/L each). Basal Salt Medium is also supplemented with modified $PTM_1$ Trace Salt Solution ($H_2SO_4$ 96% 2.5 mL; $CoC_2O_4$·$2O$ 243 mg; $CuSO_4$·$5H_2O$ 3.0 g; KI 44.5 mg; $MnSO_4$·$H_2O$ 1.5 g; $Na_2MoO_4$·$2H_2O$ 100 mg; $H_3BO_3$ 10 mg; $FeSO_4$·$7H_2O$ 32.5 g; $ZnCl_2$ 10 g; Distilled water to 500 mL)

Growth of the microorganism and expression of heterologous protein are obtained via a three steps process. A first batch growth phase (glycerol as C-source) of approx. 24 hours is followed by a fed-batch phase (glycerol as limiting C-source) of approx. 4 hours. During these first two phases, pH is maintained at 5.0 by adding $NH_4OH$ 20%. Once all the glycerol is consumed, a methanol feed is initiated to trigger the eα' protein expression and pH is shifted to 6.0 by adding $NH_4OH$ 20%. Methanol fed-batch phase lasts for approx. 24 hours. During these two fed-batch phases the Dissolved Oxygen (DO %) in maintained stable at 30% by fine electronic regulation of agitator speed (rpm), while aeration rate (vvm) is progressively increased manually. Every few hours, the C-source limiting condition is checked by following the DO % level: its value should show a sharp increase after a sudden stop of methanol feed and, vice versa, a rapid decrease after resumption of it. Every few hours, samples are taken in aseptic conditions from the fermenter for the following analyses: Optical Density (lambda 600 nm), cell biomass % (wet weight), sterility, microscopic observation, SDS-PAGE.

Purification of eα': Downstream Processing of Fermentation Broth.

About 9.2 L of culture is spilled from the fermenter and cooled on ice. All the subsequent operations are carried out at +4° C. The whole culture is separated by centrifugation (Centrikon T-124, Kontron Instruments) at 3,000× g for 30 min; biomass (pellet) is discarded; about 7.5 L of supernatant is clarified by depth filtration on Zetaplus 30SP (Cuno) and subsequently microfiltered on 0.22 μm filter (Millipak 100, Millipore). The clear filtrate is concentrated via ultrafiltration on polyethersulfone membrane, MWCO 10 kDa (Omega filter, Pall). The concentrate, about 300 mL, is diafiltered versus 3.0 L of Tris-HCl 10 mM pH 7.2 and finally lyophilized. With this procedure were obtained 34.5 g of lyophilized powder, showing rather low degree of contaminant proteins on SDS-PAGE and having a total protein content of about 25% p/p (Bradford Protein Assay, Bovine Serum Albumin as calibration standard).

Purification of eα': Chromatographic Purification

For higher performance gel electrophoresis, NuPAGE® Pre-Cast Gel System (Invitrogen) was used according to supplier's procedures. Two grams of lyophilized powder were dissolved in 150 mL 50 mM Tris-HCl, pH 7.50 and loaded on a DEAE-cellulose column (6×10 cm, Whatman, Maidstone, UK) equilibrated with the same buffer. The elution of retained proteins was carried out with the same buffer containing 150 and 250 mM NaCl respectively. The fraction eluted with 0.25 M NaCl (300 mL) displayed the greatest content of eα'. The solution was concentrated to 100 mL by freeze-drying and then dialyzed with a 6000-8000 Da membrane at 4° C. for 24 hours with milliQ ultrafiltered water and then lyophilized. About 370 mg of protein were obtained.

In order to verify the protein homogeneity, about 1 mg of protein was loaded on a Symmetry C4 (4.6×250 mm) reverse phase column. Buffer A (ultrafiltered water and Trifluoroacetic Acid 0.1%) and buffer B (Acetonitrile 100%+Trifluoroacetic Acid 0.1%) were used.

Electrophoretic Techniques.

SDS-PAGE under reducing conditions (2% β-mercaptoethanol) was carried out on 12% polyacrylamide gels, according to ref. 11, using a mini-Protean II cell (Bio-Rad). The gels were stained with Coomassie Blue.

Cell Cultures.

The established human hepatoma cell line (HepG2) was obtained from American Type Culture Collection (Rockville, Md.). Eagle's minimum essential medium (MEM), fetal calf serum, trypsin-EDTA (1×), penicillin ($10^5$ U/L), streptomycin (100 g/L), tricine buffer (1 mmol/L, pH 7.4) and non-essential amino acid solutions (100×) were from GIBCO (Madison, Wis.). Petri dishes were from COSTAR (Cambridge, Mass.). Filters were from Millipore (Bedford, Mass.). The Protein Coomassie Plus Protein Assay kit was purchased from Pierce (Rockford, Ill., USA). $^{125}$Iodine, carrier free, in 100 mmol/L NaOH, was from Perkin Elmer Life Sciences (Boston, Mass.). Sephadex G25 columns (PD10) were from Pharmacia Biotech (Uppsala, Sweden). LDH and MTT kit were from Sigma Diagnostics (Milano-Italy). All other chemicals were of analytical grade from Merck (Darmstadt, Germany). Cells were grown in monolayers in 90 mm-diameter Petri dishes, and maintained at 37° C. in a humidified atmosphere of 95% air, 5% $CO_2$ in MEM supplemented with 10% fetal calf serum (FCS), non essential amino acid solution (1%, v/v), penicillin ($10^5$ U/L), streptomycin (0.1 g/L), tricine buffer (20 mmol/L, pH 7.4), $NaHCO_3$ (24 mmol/L) and sodium pyruvate (0.11 g/L). For experiments designed to evaluate the LDL receptor modulation, cells were seeded in 35 mm plastic dishes (3-5×$10^5$ cells) and used just before reaching confluence. In all cell culture experiments, the medium was changed every 2-3 days. In order to assess cell viability, culture media from cells exposed to eα' at different concentrations were tested by methyltetrazolium salts (MTT) assay, essentially as described in ref. 9. Cell enzyme leakage was determined by measuring lactate dehydrogenase (LDH) activity, using a kinetic (LDH/LD) diagnostic kit (Sigma Diagnostics). LDL (1.019≤d≤1.063 g/L) were isolated by sequential preparative ultracentrifugation [12] from the plasma of clinically healthy normolipidemic volunteers. Lipoproteins were labeled according to the method of McFarlane as modified by Bilheimer et al. [13], and previously described [3]. $^{125}$I-LDL were sterilized by filtration (Millipore filters, 0.45 µm pore size) and stored at 4° C. until use. Human lipoprotein deficient serum (LPDS) was prepared as previously described [9].

Uptake and Degradation of $^{125}$I-LDL.

Monolayers of cells were preincubated at 37° C. for 24 h in MEM supplemented with 5 g/100 g LPDS to up-regulate the LDL-receptors [2], in the presence/absence of eα' at different concentrations listed in Table or 3.5 µmol/L α' purified subunit or 1.0 µmol/L simvastatin. A fixed concentration (7.5 mg/L) of $^{125}$I-LDL was then added to the medium and the incubation continued for a further 5 h at 37° C. Specific uptake (binding+internalization) and degradation of $^{125}$I-LDL were evaluated as previously reported [2].

Statistical Analyses.

Differences in cell uptake and degradation of LDL after cell incubation with eα' at different concentrations were determined by ANOVA followed by Dunnett's test. Values are expressed as means±SD; P values<0.05 were considered as statistically significant.

Results

Expression of eα' in *Pichia pastoris*.

The structure of the plasmid used to transform *Pichia pastoris* cells is shown in FIG. 1. The sequence of the insert and its alignment with the α' subunit are shown in FIG. 2. As mentioned in the Materials and Methods, the only difference between the recombinant and wild type polypeptides consisted in the N-terminal first amino acid residue which, for technical reasons, was an alanine in the recombinant chain. The clone showing the greatest production of recombinant polypeptide, as judged by SDS-PAGE analysis of the culture medium (not shown), was selected for massive production. FIG. 3-A shows the electrophoretic analysis of the supernatant of the yeast culture before (lane n.1) and after induction with methanol for 1-8-19 and 25 hours (lane n.2, n.3, n.4, n.5). At it is shown, an evident band at an apparent molecular weight of about 20 kDa arises as a consequence of the induction.

Purification of eα'.

The purification of eα' was achieved by chromatographic methods. Samples from each step were collected and analyzed by SDS-PAGE. The effect of the purification steps on the homogeneity of the identified polypeptide is shown in FIG. 3-B. A very low degree of contamination by yeast protein was already achieved in the culture medium, but the further chromatographic steps removed main contaminant proteins and allowed the recovery of the recombinant polypeptide in an almost homogenous form. N-terminal sequence analysis of this band confirmed that this 20 kDa polypeptide corresponded to the eα' chain. The purity of this sample was judged to be suitable for the cell assays.

Biological Activity of eα'.

The addition of the purified α' subunit, as a positive control, and its truncated α' form to HepG2 cells produced a significant rise in LDL receptor-mediated uptake and degradation compared to the untreated cells, as reported in the following Table.

TABLE

Effect of α' and its truncated form (eα') on the LDL uptake and degradation by HepG2 cells[1,2]

| Sample type | Concentration[3] µmol/L | Uptake ng$^{125}$ I-LDL/ mg cell protein | % | Degradation ng$^{125}$ I-LDL/ mg cell protein | % |
|---|---|---|---|---|---|
| LPDS[4] | — | 94 ± 5.1 | 100 | 80 ± 4.3 | 100 |
| 7S α' subunit | 3.5 | 154 ± 9.1* | 164 | 128 ± 4.8* | 160 |
| eα' | 0.5 | 113 ± 7.1* | 120 | 100 ± 10* | 125 |
|  | 1.0 | 138 ± 9.2* | 146 | 118 ± 9.3* | 148 |
|  | 2.0 | 169 ± 6.7** | 179 | 157 ± 8.7** | 196 |
| Simvastatin | 1.0 | 188 ± 10** | 200 | 143 ± 7.9** | 179 |

[1]The data are means ± SD of 3 independent experiments, each performed in quadruplicate. *P < 0.05 vs LPDS and **P < 0.001 vs LPDS
[2]Confluent monolayers of HepG2 cells were preincubated for 24 h at 37° C. in minimum essential medium with 5% LPDS, in the presence or absence of different concentrations of recombinant polypeptide (eα') or purified α' subunit (7S α') or simvastatin. After the addition of $^{125}$I-LDL (7.5 mg/L of medium), cells were incubated for an additional 5 h.
[4]LPDS, lipoprotein-deficient serum.

The results showed that the LDL modulation was dose-dependent with eα' and that the highest concentration was similar to that of the positive control, simvastatin. At no concentration of eα' was there any evidence of cellular toxicity, as determined by the MTT and LDH assays (not shown).

It has been therefore found according to the invention that the, amino acid sequence capable of inducing the biological response lies in the N-terminal extension domain of a' chain. Moreover, we found that the N-terminal hydrophilic fragment exerts its effects at concentrations in the order of magnitude as those of simvastatin, a potent hypolipidemic drug. This effect might at least partially be due to the in vitro interaction between the above fragment and thioredoxin, a small multifunctional protein with a redox-active disulfide-dithiol in the conserved active site sequence Cys-Gly-Pro-Cys (SEQ ID NO: 8), as reported by the present inventors [3]. This finding might explain the longer lag phase of LDL oxidation induced by cupric oxide observed in rabbits fed cholesterol-rich diet The data obtained are particularly interesting because they show for the first time that the N-terminal hydrophilic fragment of soybean 7S globulin α'chain is active in in vitro model at concentrations less than 10 that are similar that those reported for simvastatin. Moreover, the use of a recombinant protein rules out any involvement of other protein and non-protein soybean components, including isoflavones, for which a lack of clear benefits and potential toxicity have been reported[23].

The invention provides functional foods and compositions with beneficial effects on various diseases, including hyperlipidemia and cardiovascular disease, to be used alone or in combination with drugs in lipid-lowering therapies, i.e. statins such simvastatin, pravastatin, fluvastatin, atorvastatin, lovastatin.

The compositions of the invention are prepared using conventional excipients and methods. The dosage of the recombinant polypeptide of the invention will depend on several factors, such as patient's weight, age and sex and will be easily determined by the practitioner on the basis of pharmacodynamics, pharmacokinetics and toxicological characteristics of the polypeptide. In general, however, said dosage will range from about 50 to about 500 mg, once to three time a day.

REFERENCES

1. Sirtori C R. et al., Curr Atheroscler Rep. 2001; 3: 47-53.
2. Lovati M R. et al., J Nutr. 1992; 122: 1971-8.
3. Manzoni C. et al., J Nutr. 2003; 133: 2149-55.
4. Duranti M. et al., J Nutr. 2004; 134: 1334-39.

5. Thanh, V H. et al., Biochim Biophys Acta. 1976; 439: 326-38.
6. Maruyama N. et al., J Agric Food Chem. 1999; 47: 5278-84.
7. Sirtori C R. et al., Nutr Metab Cardiovasc Dis. 1998; 8: 334-40.
8. Lovati M R. et al., J Agric Food Chem. 1998; 46: 2474-80.
9. Lovati M R. et al., J Nutr. 2000; 130: 2543-2549.
10. Lovati M R. et al., Faseb J. 2006; LB 391: 86.
11. Laemmli U K. Nature. 1970; 227: 660-5.
12. Havel R Y. et al., J Clin Invest. 1955; 34: 1345-53.
13. Bilheimer D W. et al.,. Biochim. Biophys. Acta 1972; 260: 212-21.
14. Sirtori C R. et al., Brit J Nutr. 2007; 97: 816-22.
15. Lovati M R. et al., Nutr Metab Cardiovasc Dis. 1991; 1: 18-24.
16. Lovati M R. et al., J Clin Invest. 1987; 80: 1498-502.
17. Kitts D D. et al., Curr Pharm Des. 2003; 9: 1309-23.
18. Wan X S. et al., Nutrition and Cancer. 2002; 43:167-73.
19. Clemente A. et al., Recent Progress in Medicinal Plants. 2008; 20:397-417.
20. Matoba N. et al., FEBS Lett. 2001; 497: 50-4.
21. Cho S J. et al., J Agric Food Chem. 2008; 56: 4372-6.
22. Castiglioni S. et al., Atherosclerosis. 2003; 171: 163-70.
23. Sirtori C R. et al., Drug Safety 2001; 24: 665-82.

The invention claimed is:

1. A recombinant N-terminal hydrophilic fragment of Soybean 7S Globulin α' Subunit, wherein said recombinant N-terminal hydrophilic fragment of Soybean 7S Globulin α' Subunit consists of the amino acid sequence of SEQ ID NO: 1.

2. A process for preparing the N-terminal hydrophilic fragment of Soybean 7S Globulin α' Subunit of claim 1, comprising:

expressing a polynucleotide encoding the N-terminal hydrophilic fragment of Soybean 7S Globulin α' Subunit of claim 1 in *Pichia pastoris*, and isolating the recombinant N-terminal hydrophilic fragment.

3. A composition comprising as the active ingredient the N-terminal hydrophilic fragment of the Soybean 7S Globulin α' Subunit of claim 1 and a carrier.

* * * * *

SEQUENCE LISTING

<160> NUMBER OF SEQ ID NOS: 8

<210> SEQ ID NO 1
<211> LENGTH: 142
<212> TYPE: PRT
<213> ORGANISM: Glycine max

<400> SEQUENCE: 1

Ala Val Glu Glu Glu Glu Cys Glu Glu Gly Gln Ile Pro Arg Pro
1               5                   10                  15

Arg Pro Gln His Pro Glu Arg Glu Arg Gln Gln His Gly Glu Lys Glu
            20                  25                  30

Glu Asp Glu Gly Glu Gln Pro Arg Pro Phe Pro Phe Pro Arg Pro Arg
            35                  40                  45

Gln Pro His Gln Glu Glu Glu His Glu Gln Lys Glu Glu His Glu Trp
    50                  55                  60

His Arg Lys Glu Glu Lys His Gly Gly Lys Gly Ser Glu Glu Glu Gln
65                  70                  75                  80

Asp Glu Arg Glu His Pro Arg Pro His Gln Pro His Gln Lys Glu Glu
                85                  90                  95

Glu Lys His Glu Trp Gln His Lys Gln Glu Lys His Gln Gly Lys Glu
            100                 105                 110

Ser Glu Glu Glu Glu Glu Asp Gln Asp Glu Asp Glu Glu Gln Asp Lys
        115                 120                 125

Glu Ser Gln Glu Ser Glu Gly Ser Glu Ser Gln Arg Glu Pro
    130                 135                 140

<210> SEQ ID NO 2
<211> LENGTH: 577
<212> TYPE: PRT
<213> ORGANISM: Glycine max

<400> SEQUENCE: 2

Val Glu Glu Glu Glu Glu Cys Glu Glu Gly Gln Ile Pro Arg Pro Arg
1               5                   10                  15

Pro Gln His Pro Glu Arg Glu Arg Gln Gln His Gly Glu Lys Glu Glu
            20                  25                  30

Asp Glu Gly Glu Gln Pro Arg Pro Phe Pro Phe Pro Arg Pro Arg Gln
        35                  40                  45

Pro His Gln Glu Glu Glu His Glu Gln Lys Glu Glu His Glu Trp His
    50                  55                  60

Arg Lys Glu Glu Lys His Gly Gly Lys Gly Ser Glu Glu Glu Gln Asp
65                  70                  75                  80

-continued

```
Glu Arg Glu His Pro Arg Pro His Gln Pro His Gln Lys Glu Glu
             85                  90                  95
Lys His Glu Trp Gln His Lys Gln Glu Lys His Gln Gly Lys Glu Ser
         100                 105                 110
Glu Glu Glu Glu Glu Asp Gln Asp Glu Asp Glu Glu Gln Asp Lys Glu
         115                 120                 125
Ser Gln Glu Ser Glu Gly Ser Glu Ser Gln Arg Glu Pro Arg Arg His
     130                 135                 140
Lys Asn Lys Asn Pro Phe His Phe Asn Ser Lys Arg Phe Gln Thr Leu
145                 150                 155                 160
Phe Lys Asn Gln Tyr Gly His Val Arg Val Leu Gln Arg Phe Asn Lys
                 165                 170                 175
Arg Ser Gln Gln Leu Gln Asn Leu Arg Asp Tyr Arg Ile Leu Glu Phe
             180                 185                 190
Asn Ser Lys Pro Asn Thr Leu Leu Pro His His Ala Asp Ala Asp
         195                 200                 205
Tyr Leu Ile Val Ile Leu Asn Gly Thr Ala Ile Thr Leu Val Asn
     210                 215                 220
Asn Asp Asp Arg Asp Ser Tyr Asn Leu Gln Ser Gly Asp Ala Leu Arg
225                 230                 235                 240
Val Pro Ala Gly Thr Thr Phe Tyr Val Val Asn Pro Asp Asn Asp Glu
                 245                 250                 255
Asn Leu Arg Met Ile Ala Gly Thr Thr Phe Tyr Val Val Asn Pro Asp
             260                 265                 270
Asn Asp Glu Asn Leu Arg Met Ile Thr Leu Ala Ile Pro Val Asn Lys
         275                 280                 285
Pro Gly Arg Phe Glu Ser Phe Phe Leu Ser Ser Thr Gln Ala Gln Gln
     290                 295                 300
Ser Tyr Leu Gln Gly Phe Ser Lys Asn Ile Leu Glu Ala Ser Tyr Asp
305                 310                 315                 320
Thr Lys Phe Glu Glu Ile Asn Lys Val Leu Phe Gly Arg Glu Glu Gly
                 325                 330                 335
Gln Gln Gln Gly Glu Glu Arg Leu Gln Glu Ser Val Ile Val Glu Ile
             340                 345                 350
Ser Lys Lys Gln Ile Arg Glu Leu Ser Lys His Ala Lys Ser Ser Ser
         355                 360                 365
Arg Lys Thr Ile Ser Ser Glu Asp Lys Pro Phe Asn Leu Gly Ser Arg
     370                 375                 380
Asp Pro Ile Tyr Ser Asn Lys Leu Gly Lys Leu Phe Glu Ile Thr Gln
385                 390                 395                 400
Arg Asn Pro Gln Leu Arg Asp Leu Asp Val Phe Leu Ser Val Val Asp
                 405                 410                 415
Met Asn Glu Gly Ala Leu Phe Leu Pro His Phe Asn Ser Lys Ala Ile
             420                 425                 430
Val Val Leu Val Ile Asn Glu Gly Glu Ala Asn Ile Glu Leu Val Gly
         435                 440                 445
Ile Lys Glu Gln Gln Gln Arg Gln Gln Gln Glu Gln Pro Leu Glu
     450                 455                 460
Val Arg Lys Tyr Arg Ala Glu Leu Ser Glu Gln Asp Ile Phe Val Ile
465                 470                 475                 480
Pro Ala Gly Tyr Pro Val Met Val Asn Ala Thr Ser Asp Leu Asn Phe
                 485                 490                 495
Phe Ala Phe Gly Ile Asn Ala Glu Asn Asn Gln Arg Asn Phe Leu Ala
             500                 505                 510
```

-continued

```
Gly Ser Lys Asp Asn Val Ile Ser Gln Ile Pro Ser Gln Val Gln Glu
        515                 520                 525

Leu Ala Phe Pro Arg Ser Ala Lys Asp Ile Glu Asn Leu Ile Lys Ser
    530                 535                 540

Gln Ser Glu Ser Tyr Phe Val Asp Ala Gln Pro Gln Leu Lys Glu Glu
545                 550                 555                 560

Gly Asn Lys Gly Arg Lys Gly Pro Leu Ser Ser Ile Leu Arg Ala Phe
                565                 570                 575

Tyr

<210> SEQ ID NO 3
<211> LENGTH: 8
<212> TYPE: PRT
<213> ORGANISM: Glycine max

<400> SEQUENCE: 3

Phe Val Val Asn Ala Thr Ser Asn
1               5

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaaaagatag attaaagctg cagtggagga ag                                    32

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccttcttat tctttctaga tcatggttct ctttgagact c                          41

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gactggttcc aattgacaag c                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcaaatggca ttctgacatc c                                                21

<210> SEQ ID NO 8
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Gly Pro Cys
1
```